(12) United States Patent
Poole

(10) Patent No.: US 8,465,975 B2
(45) Date of Patent: Jun. 18, 2013

(54) HUMAN LATE STAGE MOTOR NEURON PROGENITOR CELLS PRODUCED FROM PLURIPOTENT STEM CELLS

(75) Inventor: Aleksandra Jovanovic Poole, San Marcos, CA (US)

(73) Assignee: California Stem Cell, Inc., Irvine, CA (US)

( * ) Notice: Subject to any disclaimer, the term of this patent is extended or adjusted under 35 U.S.C. 154(b) by 0 days.

(21) Appl. No.: 13/324,956

(22) Filed: Dec. 13, 2011

(65) Prior Publication Data

US 2012/0107934 A1 May 3, 2012

Related U.S. Application Data

(63) Continuation of application No. 12/054,245, filed on Mar. 24, 2008, now Pat. No. 8,137,971.

(51) Int. Cl.
*C12N 15/00* (2006.01)

(52) U.S. Cl.
USPC ........... 435/377; 435/384; 435/387; 435/395; 435/368

(58) Field of Classification Search
None
See application file for complete search history.

(56) References Cited

U.S. PATENT DOCUMENTS

2005/0095706 A1* 5/2005 Zhang et al. .................. 435/368

FOREIGN PATENT DOCUMENTS

WO WO 2006/044204 A2 4/2006

OTHER PUBLICATIONS

Schulz et al. Directed neuronal differentiation of human embryonic stem cells. BMC Neuroscience, 2003, 4:27, pp. 1-13.*
Gaulden et al. Neur-ons and neur-offs: regulators of neural induction in vertebrate embryos and embryonic stem cells. Human Molecular Genetics, 2008, vol. 17, Review Issue 1 R60-R66.*
Ben-Hur, T., et al. "Human Embryonic Stem Cells for Neuronal Repair," IMAJ, Feb. 2006, vol. 8, pp. 122-126.
Li, Xue-Jun, et al. "Specification of Motoneurons from Human Embryonic Stem Cells" Nature Biotechnology, Feb. 2005, vol. 23, pp. 215-221.
Pan, Y., et al. "In Vitro Neuronal Difereentiation of Cultured Human Embryonic Germ Cells," Biochemical and Biophysical Research Communications, 2005 (327), pp. 54-556.
Pomp, O., et al. "Generation of Peripheral Sensory and Sympathetic Neurons and Neural Crest Cells from Human Embryonic Stem Cells" Stem Cells, 2005, vol. 23, pp. 923-930.

* cited by examiner

*Primary Examiner* — Deborah Crouch
(74) *Attorney, Agent, or Firm* — Baker & Hostetler LLP; Mark Krietzman

(57) ABSTRACT

Motor neuron progenitor (MNP) cells and populations of MNP cells, are provided, in particular, populations of human late stage MNP cells having a purity of greater than about 65% late stage MNP cells and high-purity populations of MNP cells having greater than 95% viable cells, as well as method of making and using the same, including deriving late stage MNP cells from pluripotent embryonic stem cells, producing high-purity populations of late stage MNP cells, producing populations of viable MNP cells, transporting viable MNP cells, and transplanting MNP cells.

16 Claims, 3 Drawing Sheets

HUMAN LATE STAGE MOTOR NEURON PROGENITOR CELLS PRODUCED FROM PLURIPOTENT STEM CELLS

RELATED APPLICATIONS

This application claims benefit of priority of U.S. Application Ser. No. 60/896,758, filed Mar. 23, 2007, which is hereby expressly incorporated by reference, and U.S. Ser. No. 12/054,245 filed Mar. 24, 2008, which is also incorporated by reference.

FIELD OF THE INVENTION

The present disclosure relates to motor neuron progenitor (MNP) cells, populations of MNP cells having a purity greater than about 65%, and methods of making and using the same, including transporting viable MNP cells, MNP cell viability measurements, and transplanting MNP cells.

INTRODUCTION

Motor neurons are cells predominantly located in the spinal cord and have been shown to transmit information from the central nervous system to effector muscles. While numerous neurological disorders are known that involve one or more pathologic aspects of this cellular population, developments in diagnosis and/or treatment are limited due to a lack of availability of a defined motor neuron cell population.

Motor Neuron Development

The development of the spinal cord cellular population is initiated from ectodejinal formation of the neural tube. Initially the neural tube consists of neuro-epithelial cells which are organized in two regions: dorsal (the alar plate) and ventral (the basal plate). The basal plate will generate the anterior horns of the spinal cord which contain the motor neuron bodies and oligodendrocytes. The gradient from dorsal to ventral of local chemical signals is thought to be the main reason of the layering of the neuronal populations in the spinal cord. Sonic hedgehog (SHH) seems to be one of the factors involved.

Development-Specific Markers

Transcription factors expressed in motor neuron progenitors during embryogenesis include, for example, Pax6, Ngn2, Nkx6.1 and Olig1, 2, whose, expression precedes that of factors specifying motor neuron fate, including LIM homeobox transcription factors (HB9, islet1, islet2, Lhx3, Lim1, and Lim3). Mature neuronal markers specific for neurons in general include the presence of neuronal filaments (for example beta tubulin, MAP2, Tuj1), or neuronal nuclei specific protein (NeuN). More specific markers for mature motor neurons include REG2, a protein localized on the motor neuron membrane along the axons of motor neurons, survival motor neuron (SMN) protein, neurofilament SMI32 motor neuron marker, and cholinergic cell markers, such as choline acetyltransferase (ChAT) or vesicular acetylcholine transporter (VAChT).

SUMMARY OF THE INVENTION

The invention provides isolated populations of human late stage motor neuron progenitor (MNP) cells having a purity of greater than about 65% late stage MNP cells. The invention further provides isolated populations of human late stage MNP cells having a purity of greater than about 65% late stage MNP cells, wherein the contaminant population is less than about 35% astrocytes. The invention provides isolated population of human late stage MNP cells having a purity of between 65% and 99% late stage motor neuron progenitor cells. The invention provides isolated population of human late stage MNP cells having a purity of greater than about 65% late stage MNP cells, wherein teh the contaminant population is between 0% and about 35% astrocytes.

The invention provides isolated populations of human late stage MNP cells having a purity of greater than about 65% late stage MNP cells, wherein at least a portion of the cells express two or more LIM homeobox transcription factors, wherein the LIM homeobox transcription factor is HB9, Isl1, Lhx3, or Lim1. The invention provides isolated populations of human late stage MNP cells having a purity of greater than about 65% late stage MNP cells, wherein the cells have a calcium physiochemical profile typical of late stage motor neuron progenitor cells but absent from mature motor neurons. The invention provides isolated populations of human late stage MNP cells having a purity of greater than about 65% late stage MNP cells, wherein the cells express a neurofilament marker or a neuronal nuclei specific protein. The invention provides isolated populations of human late stage MNP cells having a purity of greater than about 65% late stage MNP cells, wherein, where the cells are cultured on a confluent astrocytic layer, the cells generate mature motor neurons expressing one or more of SMN, SMI32 ChAT and VAChT markers.

The invention provides isolated populations of human late stage MNP cells having a purity of greater than about 65% late stage MNP cells wherein the cells have been transformed or transfected with a nucleic acid sequence that encodes a peptide that is not typically expressed in a non-transformed or non-transfected human motor neuron. The nucleic acid sequence can encode adenylyl cyclase.

The invention provides isolated populations of human late stage MNP cells having a purity of greater than about 65% late stage MNP cells wherein the cells are characterized by the expression two or more LIM homeobox transcription factors and at least one of a neurofilament marker or a neuronal nuclei specific protein, and the absence of calcium channel activity.

The invention provides composition formulated for injection or implantation of an isolated population of human late stage MNP cells having a purity of greater than about 65% late stage MNP cells. The invention provides a test system for evaluation of a drug for treatment of a neural disease including an isolated population of human late stage MNP cells having a purity of greater than about 65% late stage MNP cells, and a drug. The test system can be a kit. The invention provides a cellular model of human motor neuron diseases using an isolated population of human late stage MNP cells having a purity of greater than about 65% late stage MNP cells. The invention provides a method of treating a patient in need of motor neuron cells, comprising administering to the patient an isolated population of human late stage MNP cells having a purity of greater than about 65% late stage MNP cells.

The invention provides methods of generating a high-purity population of late stage MNP cells wherein the population has a purity of greater than about 65% late stage MNP cells, by (a) neuralizing a culture of pluripotent stem cells by culturing pluripotent stem cells in a growth media supplemented with one or more of albumin, a fatty acid, a thyroid hormone, a growth factor, a vitamin, a trace mineral, insulin and transferrin; (b) ventralizing the neuralized cell population of step (a) in a motor neuron media supplemented with retinoic acid for at least about five days; (c) incubating the ventralized cell population of step (b) in the growth media in the absence of retinoic acid to promote formation of neurospheres; (d) selecting the neurospheres; and (e) expanding the neurospheres on an adherent substrate to form a layer of cells comprising a population of cells comprising greater than about 65% late stage MNP cells. The growth media can be a serum-free media, where the serum-free growth media can contain non-essential amino acids, dipeptide L-glutamine, pyruvate, human albumin, ethanolamine, insulin, transferrin, selenite, and T3 thyroid hormone. The growth media can be a media that does not contain bone morphogenic protein (BMP). The growth factor of the growth medium is a fibroblast growth factor. The motor neuron media can be a serum-free media. The serum-free motor neuron media can contain B27 supplement with Vitamin A, magnesium chloride, and dipeptide L-glutamine. The serum-free motor neuron media can be supplemented with retinoic acid (RA) at a concentration of between about 5 µM to about 20 µM. The serum-free motor neuron media supplemented with RA can be further supplemented with a fibroblast growth factor, wherein the fibroblast growth factor is beta fibroblast growth factor (bFGF) at a concentration of between about 2 ng/ml to about 20 ng/ml.

The neurospheres can be selected by gravitational sedimentation of the neurospheres. After the neurospheres are expanding on an adherent substrate, the layer of cells comprising a population of cells having greater than about 65% late stage MNP cells, has a purity of between 65% and 100% late stage MNP cells, and the contaminant population is less than about 35% astrocytes, where the contaminant population can be between 0% to about 35% astrocytes.

The invention provides a method for producing a high-purity population of late stage MNP cells wherein the population has a purity of greater than about 65% late stage MNP cells and contains cells characterized by the expression two or more LIM homeobox transcription factors and at least one of a neurofilament marker or a neuronal nuclei specific protein, and the absence of calcium channel activity.

The invention provides a method for evaluating a drug candidate for treatment of a motor neuron disease by contacting a high-purity pc with the drug candidate, and determining if the drug candidate modulates the activity or function of late stage MNP cells. The high-purity population of late stage MNP cells for use in the method for evaluating a drug candidate for treatment of a motor neuron disease can be obtained from a subject suffering from a motor neuron disease. The method for evaluating a drug candidate for treatment of a motor neuron disease may further include a high-purity population of late stage MNP cells obtained from a subject suffering from a motor neuron disease and a high-purity population of late stage motor neuron progenitor cells obtained from a subject not suffering from a motor neuron disease, where the method includes contacting both populations of late stage MNP cells and determining whether the drug candidate had the same or a different effect on each population.

The invention provides kits for evaluating a drug candidate for treatment of a motor neuron disease, where the kits include an isolated population of late stage MNP cells wherein the population has a purity of greater than about 65% late stage MNP cells, at least one drug candidate, and means for analyzing the activity or function of late stage MNP cells to determine if the drug candidate modulates the activity or function of late stage MNP cells.

The invention provides a method of preparing a population of viable human MNP cells by: (a) obtaining population of human late stage MNP cells having a purity of greater than about 65% late stage MNP cells, wherein the population is cultured on an adherent substrate and provides a layer of MNP cells; (b) dissociating the layer of MNP cells cultured on the adherent substrate to provide a cell suspension; (c) allowing the cell suspension to rest in a non-adherent environment for a period of time sufficient for floating microspheres containing viable cells to form; (c) selecting the floating microspheres containing viable cells; and (d) collecting the microspheres to provide a population of viable human MNP cells. The layer of MNP cells can be enzymatically dissociated. The cell suspension can be washed after dissociating. The non-adherent environment can be a low-adherent material or a material coated for minimal cell adhesion. The cell suspension can be allowed to rest for between at 6 hours and about 20 hours. The floating microspheres can be selected by gravitational sedimentation of the cell suspension, wherein the floating microspheres remain in the supernatant and the nonviable cells form a pellet, where this step can be repeated multiple times. After selecting the microspheres and discarding the pellet, the supernatant containing the microspheres can be collected to provide a population of viable human MNP cells. The number of viable and nonviable cells present per unit volume of solution can be determined after at least one step in the method. The invention provide a method for providing a population of viable human MNP cells having a purity of greater than about 65% late stage MNP cells, that contains greater than 95% viable cells.

The invention provides a method for determining number of viable cells in a population of viable human MNP cells prepared according to methods of the invention, by: (a) measuring the number of viable and nonviable cells in an sample of the cell suspension to determine the total number of viable and nonviable cells in the cell suspension; (b) measuring the number of cells in sample of discarded material after each step, to determine the total number of discarded viable and nonviable cells; and (c) determining the total number of viable cells in the supernatant containing floating microspheres, by subtracting the total number of discarded viable cells from the total number of viable cells in the cell suspension. The method can be used to determine the number of viable cells per unit volume of the supernatant.

The invention provides a method for preparing a population of viable motor neuron progenitor cells prepared according to methods of the invention, for transplantation into a subject, by: (a) determining the number of cells to be transplanted; (b) determining the volume of supernatant needed to supply the number cells to be transplanted; (c) determining the total volume to be transplanted; and (d) mixing the volume of supernatant needed to supply the number cells to be transplanted with a volume of transplant vehicle needed to achieve the total volume to be transplanted. The invention provides a method of treating a patient in need of motor neuron cell progenitors, comprising administering to the patient with a motor neuron disorder a population of human late MNP cells prepared by this method.

The invention provides a method of treating a patient in need of motor neuron cell progenitors, by administering to the patient with a motor neuron disorder a population of viable human late stage MNP cells a population having a purity of greater than about 65% late stage MNP cells, prepared according to methods of the invention.

DETAILED DESCRIPTION OF THE INVENTION

Figure 1:
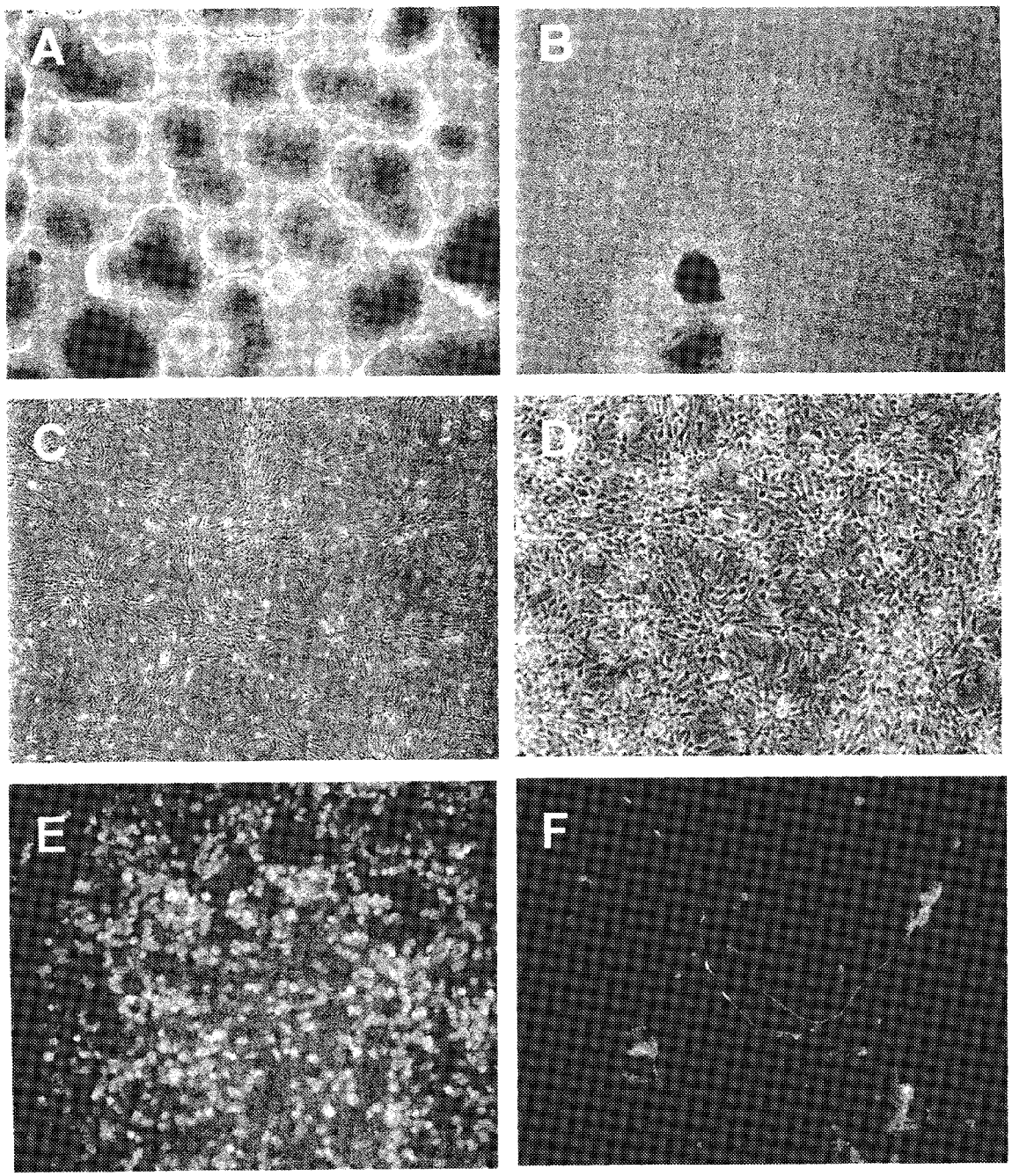
FIGS. 1A-1F show images of: A) Neurospheres in nonadherent culture conditions at approximate 14 days after ventralization; B) Plated neurospheres on adherent substrate showing migration of the early MN progenitors; C) Expansion of the ventralized neural progenitor (early MN progenitors); D) Late stage MN progenitors with branched but immature morphology; E) HB9 (pink) transcription factor marker for MN progenitors, Hoechst nuclear staining (blue); and F) Neurofilaments (Tuj1, green) and synapses (synaptophysin, red) on late stage MN progenitors.
Figure 2:
FIGS. 2A-2D show: A) Morphology of MN after extensive culture on astrocytes; B) The cellular expansions (axons and dendrites) of mature MN; C) Culture of myoblasts which fuse to form more mature syncytial myotubes; and D) MN axons make motor synapses in cocultures with myotubes.
Figure 2:
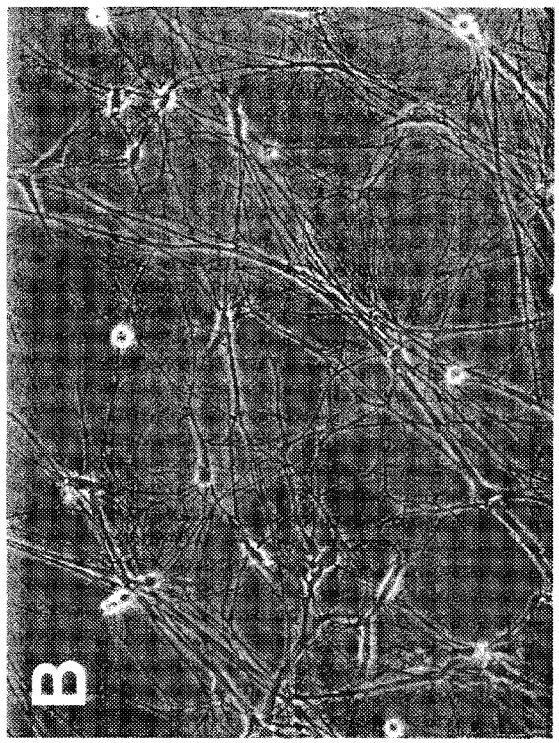
Figure 2:
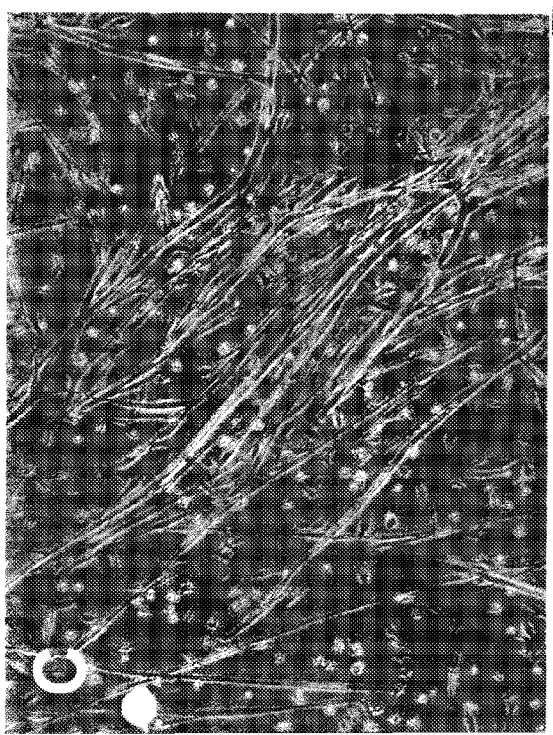
Figure 2:
Figure 3:
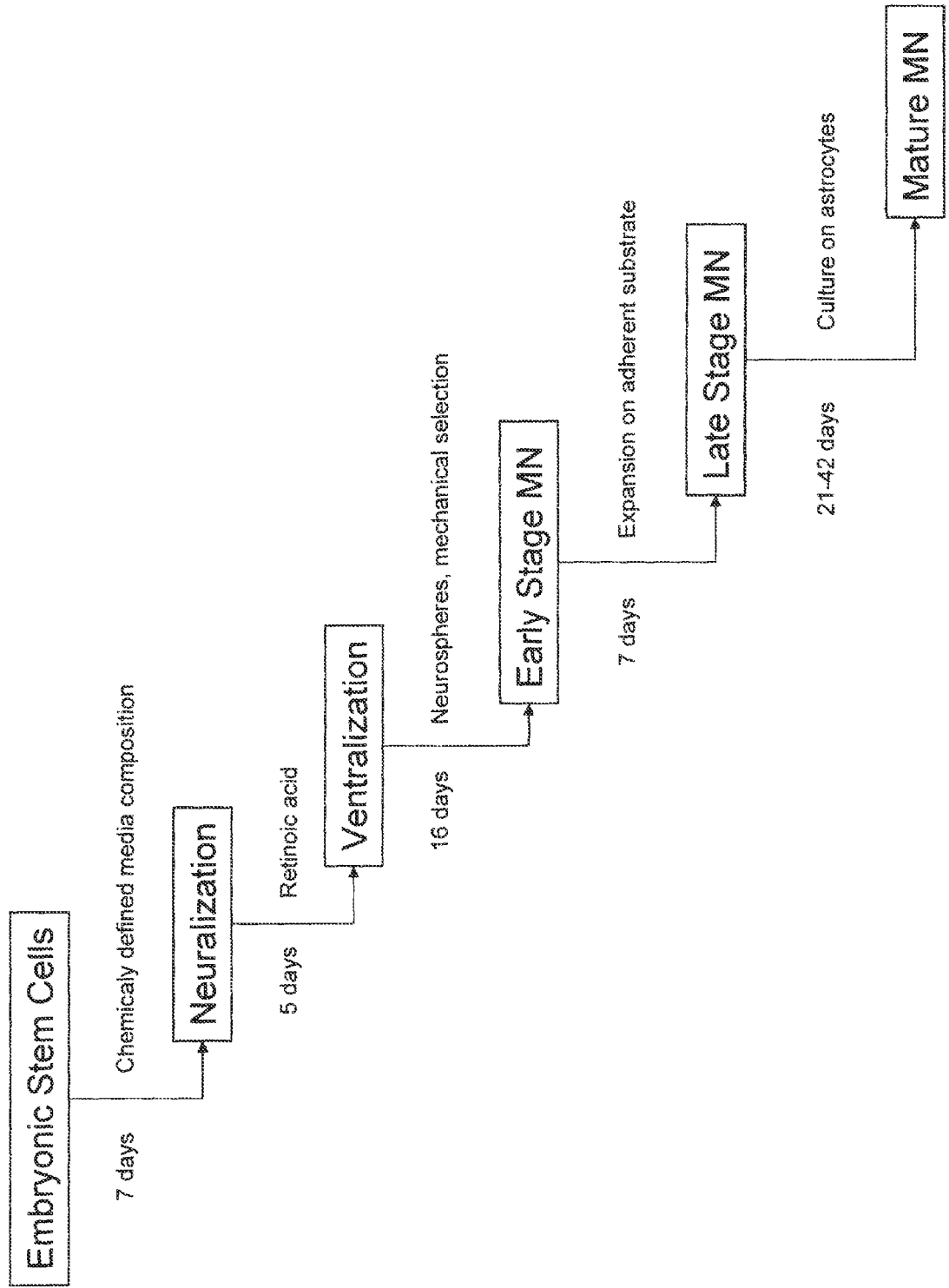
FIG. 3 shows a flowchart for production of motor neuron progenitor cells (MNP cells).

The present disclosure provides motor neuron progenitor (MNP) cells derived from embryonic stem cells, specifically, MNP cells derived from human embryonic stem cells (hESCs), where the MNP cells display known morphological and genetic characteristics of motor neuron progenitor cells, can be successfully transported live over long distances and arrive ready for use, and can be successfully transplanted into a host animal where the MNP cells integrate into spinal cord tissue. Early stage and late stage MNP cells are provided. The present disclosure provides high-purity populations of MNP cells having a purity greater than about 65% late stage MNP cells, and viability levels that can exceed about 95%.

Production of Motor Neuron Progenitor Cells

In accordance with one aspect of the invention, methods for producing motor neuron progenitor cells, in particular early stage MNP cells and late stage MNP cells, as well high-purity populations of MNP cells, are provided herein. Embryonic stem cell numbers can be expanded over multiple cell cycles, and then be induced to differentiate into common neural progenitors. Various media compositions are used to induce stem cells to produce neural cells. The present disclosure provides populations of late stage MNP cells (e.g., mammalian, such as human) characterized by a low percentage of other cells types such as astrocytes, and methods of making and using such high-purity populations of late stage MNP cells.

Without wishing to be limited by this theory, compositions and methods described herein utilize normal developmental pathways, in which stem cells begin to differentiate into broad neural progenitors in a process called neuralization, and then begin to differentiate into motor neuron progenitors following the ventralization process. After undergoing ventralization, cell populations with a high purity of motor neuron progenitors is achieved by using a chemically defined media composition, clonal expansion of the progenitors in neurospheres and optionally physical separation of the contaminant cells.

In an exemplary neuralizing step, human embryonic stem cell (hESC) cultures are first grown to confluence and passaged in a serum-free primer media formulation which lacks certain growth factors (including bone morphogenic proteins (BMPs) found in serum) and extracellular matrix components provided by feeder cells (this is sometimes called a "priming" step). Feeder cells are typically used to maintain the pluripotency of stem cells. Feeder cells secrete many uncharacterized cytokines, growth factors and extracellular matrix components. In contrast to the media used for maintenance of pluripotency, media used for motor neuron differentiation is chemically defined, such that exposure to the media components leads to differentiation of the stem cells in a neuro-ectodermal fate. In an exemplary neuralizing procedure, a chemically defined formulation comprises a classic media, for example DMEM:F12 supplemented with albumin (0.1-0.5%); fatty acids, for example linolenic, linoleic and ethanolamine; thyroid hormones and growth factors, for example, fibroblast growth factors (FGF) 1 and 2 (e.g., about 10 µg/ml); vitamins (e.g., vitamins A and B); trace minerals, for example, zinc, copper, selenium; insulin (e.g., 5-10 µg/ml) and transferrin (e.g., 10 µg/ml). A non-limiting embodiment is disclosed in Example 1 below.

In another exemplary first step, hECS cultures are first fed daily and passaged weekly in 75 cm$^2$ plastic flasks, in commonly used mouse embryonic fibroblast (MEF) conditioned media (CM) that supports the pluripotency of hESCs. In a non-limiting embodiment, CM media is a serum-free media that can contain KO-DMEM, 20% KO-Serum replacement, non essential amino acids (1×), L-Glutamine (2 mM), J3-mercaptoethanol (100 µM), and beta fibroblast growth factor (bFGF), where the CM media has been incubated overnight on a confluent and mitotically inactivated mouse embryonic fibroblast culture, and 10 ng/ml bFGF is added prior to use for the culture of hESCs. In another exemplary neuralizing procedure, a defined media is used to maintain the expansion of undifferentiated cells while avoiding the potential that could inhibit neuro-ectodermal differentiation, because media incubated on a cell culture (e.g. CM media described above) could contain uncharacterized cytokines and growth factors with unknown roles in hESC differentiation while the contents of a defined media are known. A non-limiting embodiment of a defined hESC media is disclosed in Example 3, below.

As provided herein, nutrient-rich media and the absence of BMP signaling appear to cause a tendency of the stem cell (hESC) culture to differentiate toward neuro-ectodermal phenotypes, i.e., to begin neuralization. Colonies of cells differentiating toward neuro-ectodermal phenotypes generally have poorly delimited edges, with an abundant stroma composed of many small cells with triangular or round shape and layering tendency. Some colonies will be transformed in dense rosettes of elongated or triangular cells, radially arranged. Cells in these colonies are considered to be typical neural progenitor cells resulting from the neutralization process, and can be characterized by the presence of neural-cell-specific transcription factors (e.g., Pax6) and the intermediate filament (IF) protein nestin. Populations of these neural progenitor cells are self-renewing cellular populations and can be maintained for long time periods. Expanding these neural progenitor cells over a specified time will increase the diversity of the resulting population (more cortical neurons, lots of astrocytes, fewer motor neurons and few oligodendrocytes)

In an exemplary next step toward acquiring a motor neuron fate ((after one or two passages in the formulation described above), the physical environment of the cells can be changed from an adherent substrate to a free-floating condition (cell suspension). In an exemplary embodiment, hESC cultures are dislodged from the adherent substrate using a proteolytic enzyme, e.g., trypsin (0.05-0.25%) or collagenase (1-2 mg/ml). The cell suspension is cultured for the next 21 days in low adherent glass or plastic containers.

In one exemplary ventralization procedure, the media used is identical to the previous media, and in the first 5 days, the media is supplemented with retinoic acid (RA) in dimethylsulfoxide (DMSO) and is exchanged daily. Alternately, the media can be different. Media can include RA at between about 5 µM to about 30 µM, or between about 10 M to about 20 µM, of RA at about 10 µM RA, at about 15 µM, or RA at about 20 µM, or RA at a concentration selected by one of skill in the art. Frequent exchange of the media reduces the effect of the autocrine secretion in the culture environment. The intermediate stages of the neural progenitors tend to autocontrol the differentiation in early stages, and the outcome is a mixed population of neurons, astrocytes and oligodendrocytes. The retinoic acid (RA) included with the media is a ventralizing agent. In development, ventralization refers to the migration and separation of the neural progenitors in the ventral plate of the primordial spinal cord which will generate the motor neurons and oligodendrocytes.

In another exemplary ventralization procedure, hESCs are first allowed to adapt to a "motor neuron media" by gradual substitution. In one embodiment, hESCs are allowed to adapt before the cells are dissociated, e.g. as described in Example 3, where after one or two passages in defined hESC media, the cells were transferred into media containing 50% defined hESC media and 50% "motor neuron media" (see Example 3) and allowed to adapt. After adaptation, confluent cells can be dissociated to form a cell suspension of non-adherent hESCs that are exposed to media supplemented with RA and, optionally, bFGF, to induce further differentiation toward the desired cell type. In a non-limiting embodiment in Example 3, non-adherent hESCs were exposed to "motor neuron media" supplemented with 10 µM RA and 10 ng/ml bFGF for 7 days.

Following the retinoic acid (RA) treatment, the media is exchanged, e.g. twice a week. and growth factor supplementation (e.g. FGF2 or bFGF) is continued at about 4-5 ng/ml to about 10 ng/ml. Without wishing to be limited by this theory, at this stage, less frequent media exchange should facilitate accumulation of autocrine factors important for clonal expansion of the motor neuron progenitors.

After dissociation of the adherent cultures and RA treatment (ventralization), the motor neuron progenitor (MNP) cells will begin to agglomerate in spherical formations known as "neurospheres" which continue to grow over the duration of the differentiation protocol. In an exemplary media exchange procedure, cell cultures can be sedimented (i.e., allowed to settle) or centrifuged at low gravitational force for short time, and the supernatant discarded. This procedure should remove cells which are not agglomerated in clumps and will promote the larger clumps (neurospheres) to be carried over the differentiation protocol.

After a period of neurosphere formation, a suspension of neurospheres is plated on a suitable adherent substrate for a period of expansion and further differentiation. In one exemplary embodiment, after about 3 weeks, a suspension with the spherical formations (neurospheres) are plated on adherent substrate of matrigel (MATRIGEL™ BD Biosciences), laminin, or fibronectin for another 7 days, during which time the cells migrate from the spherical formations and will cover the entire culture surface (substrate surface). The morphology then consists of elongated cells with radial arrangements reassembling rosettes. The cells are actively dividing and tend to overgrow and form multiple layers.

At this stage (expansion after ventralization), the cells are expressing some known neural progenitor markers (e.g., Pax6), while nestin expression is reduced gradually and expression of early markers for motor neuron progenitors (Olig1, Ngn2, Nkx6.1 and LIM homeobox transcription factors, e.g., Islet 1 (Isl1), Lhx3 and Lim1) increases gradually. Cells with these characteristics are considered to be early stage motor neuron progenitors.

Early stage motor neuron progenitor cells will generate more mature cells with aging of the culture, or reduction of growth factor (e.g., FGF) addition.

Further culture in absence of fibroblast growth factors (FGF) can cause more differentiation and the cell morphology can resemble known spinal cord motor neurons.

As early stage motor neuron progenitor cells mature with further culturing, the cellular morphology will change dramatically to a typical branched neuron with a small body and two or more branches (bipolar, multipolar shape), that morphologically resemble typical neurons with small cell bodies and long branches. At this stage, the cells are expressing some of the known early motor neuron markers including transcription factors specific for earlier stages (LIM homeobox transcription factors Pax6 and HB9), and more mature markers including neuronfilaments (neuronal filaments, e.g., beta tubulin, MAP2, Tuj1), and neuronal nuclei specific protein (NeuN) and are considered late stage motor neuron progenitor (MNP) cells.

In accordance with one aspect of the invention, late stage motor neuron progenitor (MNP) cells are provided that display proper multipolar morphology, lack mature neuron markers (Reg2, SMN, SMI32 ChAT and VAChT), can form intercellular connections (e.g. as described in Example 2), and cannot replicate. Calcium imaging of late stage motor neuron progenitors indicates an absence of calcium channel activity that is characteristic of mature functional motor neurons. Thus, the late stage motor neuron progenitor (MNP) cell population is uniquely characterized by the expression of the motor neuron markers HB9, Ach, Islet 1 (Isl1), Lhx3 and Lim1 and the absence of calcium channel activity.

Immunohistological analysis of maturation/differentiation of cells after ventralization allowed analysis of differentiation, stability, and contamination in a cell population. As described in Example 3 below, when a suspension of neurospheres was plated on a suitable adherent substrate for a period of expansion and further differentiation, additional samples of the suspension of neurospheres were simultaneously plated on imaging slides and grown for several days. Immunohistological analyses were performed to detect the following: motor neuron markers HB9 or Islet 1 as indicators of differentiation into motor neuron progenitor cells; an hESC marker (OCT4) as a potential indicated of hESC contamination; markers of other types of neuronal cells such as astrocytes (GFAP), as an indicator of the presence of other neuronal cells; and markers for cells of other lineages, specifically mesodermal (SMA) and endodermal cells (AFP), as an indicator that some of the original hESC cells took a different differentiation pathway. Cell karyotypes were determined as an indicator of karyotypic stability. Imaging plates were tested for mycoplasma (or, preferably, absence of mycoplasma), as an indicator of mycoplasma contamination of the cell suspension. Typically, neurosphere cell suspensions prepared and further cultured as provided herein, produced cell populations wherein greater than about 75% of the cells expressed the motor neuron marker HB9 or Isl1, about 2% of the cells expressed the hESC marker OCT4, about 15% expressed the astrocyte marker GFAP, about 4% expressed the mesodermal marker SMA, about 4% expressed the endodermal marker AFP, wherein the cells had stable karyotypes (46, XX or 46, XY) and no mycoplasma contamination was detected. Further in accordance with an aspect of the invention, only cell suspensions having the afore-recited properties, were considered to be high-purity populations of motor neuron progenitors and released for further use.

In a non-limiting embodiment disclosed in Example 3, images for immunohistological analysis of a population of MNP cells on day 23 of differentiation, showed strong staining for Islet 1 (Isl1) and HB9, weak or no staining for OCT4, GFAP, SMA, and AFP, and negative test for mycoplasma, where cell counts of the cells (from a 46, XX human female), showed 99% of the cells staining positive for motor neuron markers HB9 or Islet 1 (Isl1), 0% staining positive for the hESC marker OCT4, 0% staining positive for the astrocyte marker GFAP, 1% staining positive for the mesodermal marker SMA, and 0% staining positive for the endodermal marker AFP, thus confirming an isolated population of human late stage MNP cells having a purity of greater than about 65% late stage MNP cells.

Optionally, clumps or aggregates of the late stage MNP cells can be dissociated and used in applications such as transplants, or other in vitro manipulations including maturation.

In accordance with another aspect of the invention, late stage MNP cells as provided herein can be genetically manipulated to introduce a nucleic acid sequence in the genome, where the sequence may be a nucleic acid sequence that is not found in the normal motor neuron cells (e.g. a promotor not normally found in motor neuron cells), or a nucleic acid sequence involved in expressing a gene product which is not found in the normal motor neuron cells, such as a peptide (e.g., an enzyme, structural protein, or transcription factor) that is not typically expressed in a non-transformed or non-transfected human motor neuron. In one non-limiting example, such a sequence could encode adenylyl cyclase which is expected to cause the rapid growth and extension of the axon. In other non-limiting examples, introduced DNA sequences could have externally controlled functions if introduced in promoter areas of genes, for example the tetracycline inducible gene (TetOn/TetOff).

Further as provided herein, late stage MNP cells can be plated on a confluent astrocytic culture after proteolytic dissociation. Late stage MNP plated on confluent astrocytes gradually mature and gradually express some of not all of the markers that were lacking in the previous stage (Reg2, SMN, SMI32 ChAT and VAChT). The cellular expansions (axon and dendrites) are very long; the cellular body is polygonal and axons can make motor junctions with muscle cells. The mature motor neurons are sensitive to manipulation: they have low tolerance to enzymatic dissociation or rupture of the branches. Late stage motor neuron progenitors that have been cultured on an astrocyte monolayer for at least 14 days in the absence of growth factors, express HB9, Ach, Isl1 and calcium channel activity, characteristic for a mature phenotype and differentiating them from the late stage motor neuron progenitors.

In accordance with another aspect of the invention, a cell population enriched in late stage MNP cells (a high-purity: population of MNP cells) is provided herein, prepared by neuralizing (limiting to a neural fate) and ventralizing induced human stem cells with retinoic acid (RA) over at least five days. The neuralized and ventralized cells are then cultivated under conditions to generate neurospheres, and the neurospheres are then expanded on a medium to form a monolayer of cells that are committed to a motor neuron lineage. When the cell types of the resulting population are identified, the population is found to contain at least about 65% MNP cells, typically more than about 85%, with best results approaching 99.5% early and late stage MN progenitors (MNP cells). That is, the resulting population is a high-purity population having a purity of greater than about 65%, or greater than about 70%, or greater than about 75%, typically more than about 85%, with best results approaching 99.5% early and late stage MNP cells.

Astrocytes are the principal contaminant which could represent up to about 35% of the cells, but are typically less than about 15 percent. Other contaminant cells including oligodendrocytes and other types of neurons represent less than 10%, typically less than 1%.

The present disclosure thus provides an isolated population late stage MNP cells, in particular human MNP cells, having a purity greater than about 65%, and further provides an isolated population late stage MNP cells, in particular human MNP cells, having a purity greater than about 65%, and a contaminant population of less than about 35% astrocytes. Further as provided herein, the isolated isolated population late stage MNP cells, in particular human MNP cells, can have a purity of between 65% and 99%, or between 65% and 100%, where such populations can have a purity of about 70%, about 75%, about 80%, about 85% about 90%, about 95%, or any purity of between 65% and 100% late stage MNP cells that is measured in a particular embodiment. The an isolated population late stage MNP cells, in particular human MNP cells, having a purity greater than about 65% as provided herein, can be referred to as high-purity populations of late stage MNP cells. Table 1 below provides a non-limiting summary of procedures that can used for generating late stage motor neuron progenitors (late stage MNP cells) of the present invention.

TABLE 1

Generalized procedures for generating late stage MNP cells

| Stage | HESc priming (neuralization) | Ventralization | Neurospheres | Expansion | Expansion or use |
|---|---|---|---|---|---|
| Media and feeding | Serum-free media (SF), daily | SF daily | SF M-W-F | SF M-W-F | SF M-W-F |
| Substrate | Matrigel | Nonadherent | Nonadherent | Matrigel | Matrigel |
| Supplements | bFGF 10 ng/ml | bFGF 10 ng RA 10 μM | bFGF 10 ng | bFGF 10 ng | bFGF 10 ng |
| Duration | 7 days | 5 days | 16 days | 7 | |
| Elapsed Time (days) | 7 | 12 | 28 | 35 | |

Preparation of High-Purity Populations of MNP Cells With High Levels of Viability In accordance with another aspect of the invention, high-purity populations of MNP cells, including high-purity populations of late stage MNP cells, having high levels of viable cells, are provided. The term "high levels of viable cells" is understood to refer to any measurement of the number, percentage, fraction, proportion, ratio, or any other measure of the viable cells present in a population of cells, where the viable cells may be measured directly or indirectly, using methods described herein or methods known in the art. High-purity populations of MNP cells, including high-purity populations of late stage MNP cells, having high levels of viable cells, as provided herein, may have viability levels of between about 90% viable cells, up to 100% viable cells, where the population may have about 91%, about 92%, about 93%, about 94%, about 95%, about 96%, about 97%, about 98%, about 99% or 100% viable cells. In one exemplary embodiment, high-purity populations of MNP cells, including high-purity populations of late stage MNP cells, are providing having greater than about 95% viabile cells.

In accordance with another aspect of the invention, methods of preparing a population of viable human MNP cells are provided. In an exemplary embodiment, a high-purity population of human late stage MNP cells having a purity of greater than about 65% late stage MNP cells cultured on an adherent substrate and forming a layer of cells, is dissociated to provide a cell suspension, and the cell suspension is allowed to rest in a non-adherent environment for a period of time sufficient for floating microspheres containing viable cells to form, after which time the floating microspheres comprising viable cells are selected by separating the microspheres from non-aggregated cells, where collecting the microspheres provides a population of viable human motor neuron progenitor cells. Without wishing to be limited by this theory, this exemplary embodiment provides an indirect method for positively selecting viable cells to provide a population of viable human MNP cells, where late stage MNP cells do not replicate such that total cells numbers are not expected to change. Without wishing to be limited by this theory, this exemplary embodiment further provides an indirect, non-invasive method of measuring the level of viable cells at any time during the preparation of the population of viable human MNP cells. Methods for positively selecting viable cells to provide a population of viable human MNP cells as provided herein, whereby all or almost all the desired viable cells are retained in each step, not only provides a population having very high levels (e.g., between 95% to 100%) of viable cells, but also avoids potential damage from other art-known methods for separating viable cells from nonviable (dead) cells using labels such as dyes or markers (.e.g, fluorescent labels such as FITC, or magnetic labels) to label viable and/or nonviable cells, and avoids mechanical trauma from cell sorting/separation procedures such as cell sorting by flow cytometry (e.g., to separate FITC-labelled viable cells) or magnetic sorting to capture cells with magnetic labels.

The layer of motor neuron progenitor cells can be enzymatically dissociated, e.g., using trypsin or trypsin replacement (TrypLE (Invitrogen, Carlsbad, Calif.)), to provide a cell suspension. In an exemplary embodiment of preparing a population of viable human motor neuron progenitor cells, the cell suspension can be washed prior to subsequent steps, using the same media (without enzyme) or a different media, by methods such as sedimentation by gentle centrifugation to obtain a cell pellet that can be washed and resuspended. The cell suspension is allowed to rest in a non-adherent environment that can be, but is not limited to, an ultra-low-binding culture dish such as CORNING® COSTAR®, Grenier CELLCOAT®, NUNC® Microwell, NUNCLON™D, or TPP multiwell plates (Sigma-Aldrich, St. Louis Mo.). The cell suspension is allowed to rest for a period of time sufficient for floating microspheres (clumps, agglomerates, aggegates) containing viable cells to form, which is generally understood to be a minimum time of about 6 hours, and a maximum time of about 20 hours, although longer or shorter periods may be appropriate for a particular embodiment.

In an exemplary embodiment of preparing a population of viable human MNP cells, the floating microspheres can be selected by gravitational sedimentation of the cell suspension to separate the floating microspheres containing viable cells, from dead cells or nonadherent viable cells that have not formed microspheres. For example, the microspheres containing viable cells can be selected by one or more cycles of gentle centrifugation, where the floating microspheres containing viable cells (i.e., agglomerates of adherent viable cells) will remain in the supernatant and the pellet will contain nonviable (dead) cells, and may also contain nonadherent viable cells that did not form microspheres. After sedimentation, the supernatant containing the floating microspehres is collected to provide a population of viable human MNP cells. The floating microspheres under multiple rounds of selections, where gravitational sedimentation of the cell suspension containing floating microspheres is subjected to gravitational sedimentation in the first round, and the supernatant of the first sedimentation is collected, followed by second and subsequent rounds of selecting by sedimentation of the supernatant collected from the prior sedimentation, and collecting the supernatant of the second sedimentation, and so on. In one embodiment, three rounds of selecting is carried out.

During the preparation of a population of viable human MNP cells, cell viability levels can be assessed at any time, as frequently as desired, by determining the number of viable and nonviable cells present per unit volume of solution. In one non-limiting embodiment as described in Example 5 below, the number of viable cells in a sample of washed cell suspension is determined using the Trypan blue exclusion assay. In the non-limiting embodiment as described in Example 5 below, the number of viable cells present in each subsequent step is calculated by relying on the initial measurement, and tracking the number of viable cells in each step by tracking sample volumes, dilutions, etc.. Furthermore, because the number of cells per unit volume can be calculated (see Example 5), one of skill in the art can determine how much sample volume to use in order to provide the desired number of viable cells for a particular use. Similarly, because the number of viable cells per sample is known, sample volumes can then be adjusted as desired, without having to assay the sample to determine the number of viable cells. Without wishing to be limited by this theory, such an indirect method for determining the level of cell viability relies on retaining all or almost all of the desired viable cells in each step, and removing nonviable (dead), or nonadherent viable cells, by means that do not harm the desired viable cells.

Transportation of MNP Cells

The present disclosure provides transportation of motor neuron progenitor (MNP) cells according to the present invention, for use at a site other than the site where the cells were produced, preferably where such cells are transported live and arrive ready for use. Transportation of live cells as provided herein avoids any potential deleterious effects associated with freezing cells, transporting frozen cells, thawing frozen cells, and preparing thawed cells for use.

In exemplary embodiments, different formats, transport conditions, and carriers were evaluated for overnight delivery from site where the MNP cells were generated, to a delivery site where the cells were evaluated. In specific non-limiting embodiments described in the Examples below, live MNP cells were transported from California to destinations in the US or Europe, over two consecutive days, under conditions as described herein.

Formats for transportation of viable MNP cells can be selected according to circumstances of each embodiment such as transport conditions and intended use of the transported cells. Formats for transportation of viable MNP cells must provide conditions that result in acceptable levels of cell survival and cell health, and do not result in unacceptable changes in the MNP cells.

Formats for transportation of viable MNP cells must provide a suitable substrate to which MNP cells or mature motor neuron cells can be adherent. Without wishing to be limited by this theory, any substrate suitable that would allow integrin should be a suitable substrate for transportation of viable MNP cells. A non-limiting list of substrates known to be suitable for transport of viable MNP cells includes MATRI-GEL™ (BD Biosciences, Franklin Lakes, N.J.), laminin, poly-L-lysine, or fibronectin. Additional suitable substrates include, but are not limited to, synthetic substrates such as hydrogels (e.g., PURAMATRIX™ peptide hydrogels, BD Biosciences), MYLAR™, TEFLON™, laminin-derived synthetic peptide, PA22-2, aminated (amine-derivatized) polyorganosiloxane, ULTR-WEB™ nanofiber surface (Corning Life Sciences, Corning N.Y.), or synthetic hydroxyapatite (HA).

Cell container formats can be selected according to the circumstances of each embodiment such as transport conditions and intended use of the transported cells. In accordance with one aspect, viable MNP cells are transported in flasks suitable for cell culture, e.g. as adherent cultures on substrate, optionally topped with media to avoid foaming and mechanical dissociation of attached cells. In accordance with another aspect, multi-well plates pre-seeded with viable MNP cells on substrate in the wells, with media as needed, are transported under conditions for transport and delivery of live cells as described herein. Multi-well plate formats as provided herein can be chosen to provide viable MNP cells ready for immediate use, e.g., sampling, imaging, or other manipulations such as high-throughput screening using robotic or manual handling for uses including but not limited to drug discovery and predictive toxicology. Non-limiting embodiments include the use of commercially available plates suitable for cell culture having, e.g., 4, 6, 8, 10, 12, 24, 36, 60, 72, 96, 384, or 1536 wells, or any other number of wells to be selected by one of skill in the art based on the design and constraints of each embodiment. Multi-well plates pre-seeded with MNP cells could be used for high-throughput and high-content screening, e.g., using small molecule libraries, siRNA libraries, adenoviral transfection vectors, or gene-based microarray approaches, to identify various therapeutic and motor neuron liability targets. Pre-plated MNP cells in multi-well plates would allow direct high-throughput measurements of cell contents and the results of interventions such as screening (see above), by means of, e.g., fluorescent reporter dyes and/or biomarkers for cell health and morphological phenotype, expression of fluorescent reporter proteins, various FRET approaches and direct measurement of electrophysiological currents in live cells.

Transportation of viable MNP cells optionally includes means for controlling temperature during transport. In exemplary embodiments for controlling temperature, cell containers (flasks or multi-well plates containing MNP cells) are surrounded by insulating or other temperature-controlling material to ensure temperature within an acceptable range, e.g. phase exchange isothermal packs to ensure a constant 20-30° C. Temperature recording devices are optionally included were packed with the cell containers to record temperatures during transport. Viability, or other measures of cell function, can be assessed before shipping and after delivery, to evaluate the effect of transportation conditions, as well as substrate and container (vessel) format, on on survival and viability of MNP cells. In non-limiting embodiments, temperatures of temperature-controlled containers containing MNP cells were measured during transport, and the temperature-controlled containers containing MNP cells maintained temperatures of about 25° C., with occasional variations in temperature remaining within the range of between about 20° C. to about 30° C. In non-limiting embodiments, MNP cell survival in temperature-controlled containers containing MNP cells was measured for MNP cells plated on different substrates. In one non-limiting embodiment, MNP cell survival was measured on Day 0, Day 1, Day 2, Day 3, and Day 4, for temperature-controlled containers containing MNP cells plated on polylysine (PolyLys), MATRIGEL™, or pallamin that were shipped, and for "control" temperature-controlled containers containing MNP cells plated on polylysine or MATRIGEL™ that were not shipped. When cell viability was measured by the MTT assay, whereby reduction of MTT ([3-(4,5-dimethylthiazol-2-yl)-2,5-diphenyl tetrazolium bromide]) is measured at 550 nm as an indicator of cell metabolic activity, "control" and "shipped" containers containing MNP cells showed acceptable levels of cell viability for time periods measured up to about 4 days.

It is further understood that MNP cells of the present invention can, if desired, be frozen, transported in a frozen state, and thawed before use, according to techniques and procedures that are well known in the art. One of skill in the art can determine when it would be desirable to transport MNP cells of the present invention in a frozen state, to be thawed before use.

Uses of Motor Neuron Progenitor Cells

In accordance with one aspect of the invention, uses for MNP cells, including high-purity populations of MNP cells having a purity greater than about 65% late stage MNP cells, are provided here, where uses can include but are not limited to: studying human motor neuron development and function (e.g., stages of maturation, interaction with other cell populations in co-culture or after transplantation); identifying and characterizing secreted products of human motor neurons (i.e. acetylcholine, survival MN protein); investigating the regenerative properties of motor neurons for developing regenerative therapy in humans; developing cellular models of human motor neuron diseases; to screen compounds in drug discovery systems (e.g., by testing of small molecule libraries for their action on motor neurons); and evaluating a drug candidate for treatment of a motor neuron disease. It is understood that MNP cells as provided herein, including high-purity populations of MNP cells having a purity greater than about 65% late stage MNP cells, may be used as surrogate indicators of actual or potential responses of motor neurons. It is further understood that high-purity populations of MNP cells having a purity greater than about 65% late stage MNP cells, may be used as surrogate indicators of actual or potential responses of motor neurons in a subject.

In accordance with another aspect of the invention, MNP cells can be used in vivo, ex vivo, and in vitro. MNP cells can be used for therapeutic applications including but not limited to transplantation of MNP cells into a subject. Additional uses of MNP cells can be determined by one of skill in the art.

In one exemplary embodiment, the use of MNP cells in applications such as drug discovery preferably uses high-purity populations of MNP cells having a purity greater than about 65% late stage MNP cells as provided herein, to ensure that the responses of MNP cells could be unambiguously detected. Without wishing to be limited by this theory, drug discovery using low purity cell populations having a mixture of different cell types that may have different responses than MNP cells, may not be successful for identifying compounds having specific and/or defined activities towards motor neurons. In another exemplary embodiment, therapeutic uses of MNP cells would require high-purity cell populations, both to maximize the number of MNP cells being administered and to minimize or eliminate administration of unwanted cell types.

In accordance with one aspect of the invention, MNP cells can be used in cellular models of human motor neuron disease, where such models could be used for basic research and drug discovery, e.g., to find treatments for motor neuron diseases or disorders including but not limited to: amyotrophic lateral sclerosis (ALS), also called Lou Gehrig's disease or classical motor neuron disease; progressive bulbar palsy, also called progressive bulbar atrophy; pseudobulbar palsy; primary lateral sclerosis (PLS); progressive muscular atrophy; spinal muscular atrophy (SMA, including SMA type I, also called Werdnig-Hoffmann disease, SMA type II, and SMA type III, also called Kugelberg-Welander disease); Fazio-Londe disease; Kennedy disease, also known as progressive spinobulbar muscular atrophy; congenital SMA with arthrogryposis; or post-polio syndrome (PPS). In an exemplary embodiment, somatic cell nuclear transfer can be used to insert DNA from a patient with a genetic defect in their motor neurons, into an oocyte, followed by the isolation of a human embryonic stem cell line, followed by the differentiation of that line into a high-purity population of MNP cells.

In accordance with another aspect of the invention, MNP cells can be used for studying exogenous diseases and disorders of motor neurons. In one exemplary embodiment, high-purity population of MNP cells can be used to study viral infections of motor neurons such as polio.

In accordance with another aspect of the invention, methods for evaluating a drug candidate for treatment of a motor neuron disease are provided, wherein a high-purity population of late stage MNP cells having a purity greater than about 65% late stage MNP cells is contacted with the drug candidate, and it is determined whether the drug candidate modulates the activity or function of late stage MNP cells. In one embodiment, the high-purity population of late stage MNP cells is obtained from a subject suffering from a motor neuron disease. In another embodiment, the method for evaluating a drug candidate includes evaluating the effect on a high-purity population of late stage MNP cells obtained from a subject suffering from a motor neuron disease, and evaluating the effect on a high-purity population of late stage MNP cells obtained from a subject not suffering from a motor neuron disease, and determining whether the drug candidate had the same or a different effect on each population. The present disclosure further provides a kit for evaluating a drug candidate for treatment of a motor neuron disease, wherein the kit contains, inter alia, at least one high-purity population of late stage MNP cells, at least one drug candidate, and means for analyzing the activity or function of late stage MNP cells to determine if the drug candidate modulates the activity or function of late stage MNP cells.

It is understood that "contacting" or "is contacted" or grammatical equivalents, can include direct contact with the late stage MNP cell, e.g. by physical interaction of the drug candidate with the cell; and can also include indirect interactions is where a drug candidate acts upon an intermediary molecule which in turn acts upon the late stage MNP cell.

It is understood that "modulates the activity or function of late stage MNP cells" refers to detecting effects on cell activity or function that has been determined to be relevant to a particular use of the MNP cells of the present invention. One of skilled in the can determine the activity (activities) or function(s) to be detected when MNP cells are being used as surrogate indicators of actual or potential activity or function of motor neurons. Exemplary embodiments include, but are not limited to, measuring viability, cell respiration, mitchondrial activity, membrane integrity, or expression of markers associated with certain conditions. For example, the MTT assay, whereby reduction of MTT([3-(4,5-dimethylthiazol-2-yl)-2,5-diphenyl tetrazolium bromide]) is measured at 550 nm, can be used as an indicator of cell metabolic activity, where a high-purity isolated population of late stage MNP cells is contacted with the drug candidate, and the MTT assay is used to determine if the drug candidate modulates the activity or function of late stage MNP cells. For example, in an in vitro model of ALS wherein superoxide dismutase (SOD) is implicated in motor neuron cell death, one of skill in the art could measure the SOD activity, cellular oxidative stress, and cytochrome c release, as well as mitochondrial antioxidative activity or oxygen free radical propagation, which may have roles in preventing mutant SOD 1-mediated motor neuron cell death, of MNP cells. Accordingly, a drug candidate could be evaluated for its effect on SOD-related mitochondrial dysfunction in MNP cells, by contacting MNP cells with the drug candidate and measuring any modulation of the "activity or function of late stage MNP cells" determined to be indicative of SOD-related mitochondrial dysfunction.

In accordance with another aspect of the invention, kits, including MNP cells, as well as populations of MNP cells enriched or selected for any developmental, maturation or differentiation stage, packaged into suitable packaging material, are provided. In various non-limiting embodiments, a kit includes a MNP cell population that immature MNP cells, early stage MNP cells, late stage MNP cells, or a mixed population thereof. In various aspects, a kit includes instructions for using the kit components e.g., instructions for performing a method of the invention, such as culturing, expanding (increasing cell numbers), proliferating, differentiating, maintaining, or preserving MNP cells, or a MNP cell-based therapy. In various aspects, a kit includes an article of manufacture, for example, an article of manufacture for culturing, expanding (increasing cell numbers), proliferating, differentiating, maintaining, or preserving MNP cells, such as a tissue culture dish, tube, flask, roller bottle or plate (e.g., a single multi-well plate or dish such as an 8, 16, 32, 64, 96, 384 and 1536 multi-well plate or dish). In additional various aspects, a kit includes an article of manufacture, for example, an article of manufacture for delivering, introducing or transplanting MNP cells into a subject locally, regionally or systemically.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions, for example, practicing a method of the invention. Thus, in additional embodiments, a kit includes a label or packaging insert including instructions for practicing a method of the invention in solution, in vitro, in vivo, or ex vivo. Instructions can therefore include instructions for practicing any of the methods of the invention described herein. For example, MNP cells can be included in a tissue culture dish, tube, flask, roller bottle or plate (e.g., a single multi-well plate or dish such as an 8, 16, 32, 64, 96, 384 and 1536 multi-well plate or dish) together with instructions for culturing, expanding (increasing cell numbers), proliferating, differentiating, maintaining, or preserving MNP cells. In an additional non-limiting example, MNP cells can be included in a container, pack, or dispenser together with instructions for administration to a subject to treat a disorder or disorder involving motor neurons as described herein. Instructions may additionally include indications of a satisfactory clinical endpoint or any adverse symptoms or complications that may occur, storage information, expiration date, or any information required by regulatory agencies such as the Food and Drug Administration for use in a human subject.

The instructions may be on "printed matter," e.g., on paper or cardboard within the kit, on a label affixed to the kit or packaging material, or attached to a tissue culture dish, tube, flask, roller bottle, plate (e.g., a single multi-well plate or dish such as an 8, 16, 32, 64, 96, 384 and 1536 multi-well plate or dish) or vial containing a component (e.g., MNP cells) of the kit. Instructions may comprise voice or video tape and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media. Invention kits can additionally include cell growth medium, buffering agent, a preservative, or a cell stabilizing agent. Each component of the kit can be enclosed within an individual container or in a mixture and all of the various containers can be within single or multiple packages.

MNP cells, as well as populations of MNP cells including MNP cells of any developmental, maturation or differentiation stage thereof, in particular populations of late stage MNP cells having a purity of greater than about 65% late stage MNP cells, can be packaged in dosage unit form for administration and uniformity of dosage. "Dosage unit form" as used herein refers to physically discrete units suited as unitary dosages; each unit contains a quantity of the composition in association with a desired effect. The unit dosage forms will depend on a variety of factors including, but not necessarily limited to, the particular composition employed, the effect to be achieved, and the pharmacodynamics and pharmacogenomics of the subject to be treated.

MNP cells as well as populations of MNP cells as provided herein, can be included in or employ pharmaceutical formulations. Pharmaceutical formulations include "pharmaceutically acceptable" and "physiologically acceptable" carriers, diluents or excipients. The terms "pharmaceutically acceptable" and "physiologically acceptable" mean that the formulation is compatible with pharmaceutical administration. Such pharmaceutical formulations are useful for treatment of, or administration or delivery to, or transplant into, a subject in vivo or ex vivo. Pharmaceutical formulations can be made to be compatible with a particular local, regional or systemic administration or delivery route. Thus, pharmaceutical formulations include carriers, diluents, or excipients suitable for administration by particular routes. Specific non-limiting examples of routes of administration for compositions of the invention are parenteral, e.g., intravenous, intraarterial, intradermal, intramuscular, subcutaneous, intra-pleural, transdermal (topical), transmucosal, intra-cranial, intra-spinal, intraocular, rectal, oral (alimentary), mucosal administration, and any other formulation suitable for the treatment method or administration protocol.

Transplantation of MNP Cells

In accordance with one aspect of the invention, late stage MNP cells, including high-purity populations of late stage MNP cells, in particular high-purity populations of late stage MNP cells having greater than about 95% viable cells, can be used for transplantation into a subject. In accordance with one aspect, the survival of the transplanted late stage MNP cells, and integration into the host, can be evaluated. In a non-limiting embodiment described in Example 6, motor neuron progenitor (MNP) cells were transplanted into the spinal cord of a mouse model of ALS, i.e., the SOD G93A mouse carrying a transgene that codes for the human SOD1 mutation that is associated with a familial form of ALS, wherein the transgene sequence has been mutated from glycine to alanine at amino acid position 93. As described in Example, 6, late stage MNP cells as provided by the present invention were transplanted into the spinal cord grey matter of the SOD1 mouse model of ALS, and immunohistochemical analyses on animal spinal cord tissue performed at 28 or 56 days after transplantation showed that the transplanted late stage MNP cells had survived and maintained their identity, and had not exhibited undesirable migration away from the site of transplantation (injection site). For example, as described in Example 6, cells were found no farther than about 1.5 mm from the expected transplantation site, where the 1.5 mm displacement was not inconsistent with a hypothesis of pressure-driven displacement during transplantation or integration. Analysis of blood, liver, spleen, lungs, muscle of mice that received transplanted late stage MNP cells did not show any late stage MNP cell markers, confirming that the transplanted late stage MNP cells did not migrate from the transplantation site.

It is understood that late stage MNP cells as provided herein, including high-purity populations of late stage MNP cells, in particular high-purity populations of late stage MNP cells having greater than about 95% viable cells, can be used for transplantation into any tissue of interest, where such tissues could be neural tissues (central nervous system or peripheral nervous system, e.g. spinal cord, nerve bundles, motor nerves, nerve ganglia, usw.) or non-neural tissues (muscle, liver, lungs, usw.). Late stage MNP cells or populations thereof, can be transplanted into the spinal cord at any position from the cervical to lumbar regions. One of skill in the art can determine what procedures would be necessary for transplanting late stage MNP cells or populations thereof, into a particular position in the spinal cord, e.g., in some embodiments, a laminectomy may be appropriate to facility entry to the spinal cord, while in other embodiments the cells could be administered by directly accessing the spinal cord, as may be possible for neonatal applications, or administration to adult subjects by inserted the injection apparatus between vertebral bodies (similar to a spinal tap).

In accordance with one aspect of the invention, when late stage MNP cells, or populations thereof, are used in a therapeutic application wherein the cells are expected to exhibit functions similar or identical to motor neuron functions, the cells are transplanted using procedures to target the cells to selected sites. In an exemplary embodiment, when cells are introduced into the spinal cord, the cells may be targeted to spinal cord grey matter, including the dorsal or ventral horn of the grey matter. In another exemplary embodiment, cells can be targeted to other sites including, but not limited to, an emerging ventral or dorsal root, a dorsal root ganglion, a spinal nerve, a peripheral nerve a motor nerve, or any other appropriate site as determined by one of skill in the art.

Unless otherwise defined, all technical and scientific terms used herein have the same meaning as commonly understood by one of ordinary skill in the art to which this invention relates. Although methods and materials similar or equivalent to those described herein can be used in the practice or testing of the invention, suitable methods and materials are described herein.

All publications, patents, Genbank accession numbers and other references cited herein are incorporated by reference in their entirety. In case of conflict, the present specification, including definitions, will control.

As used herein, singular forms "a", "and," and "the" include plural referents unless the context clearly indicates otherwise. Thus, for example, reference to a "late stage MNP cell" includes a plurality of late stage MNP cells, or a population of late stage MNP cells, and reference to "a population of late stage MNP cells having a purity of greater than about 65% late stage MNP cells" can include multiple cell types of varied developmental, maturation or differentiation stage within the population; likewise, reference to cell cultures or cell suspension during production of late stage MNP cells or a population of late stage MNP cells having a purity of greater than about 65% late stage MNP cells, can include multiple cell types of varied developmental, maturation or differentiation stage within the population.

A "subject" can be any animal, in particular a human. A "patient" can be any animal, in particular a human.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes any numerical value or range within or encompassing such values, such as 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and any numerical range within such a range, such as 90-92%, 90-95%, 95-98%, 96-98%, 99-100%, etc. In an additional example, reference to greater or less than a particular percent, e.g., greater than 25% means 26%, 27%, 28%, 29%, 30%, 31%, . . . etc.; and less than 25% means 24%, 23%, 22%, 19%, 18%, 17%, . . . etc.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

Production of MNP Cells

Briefly, human embryonic stem cell (hESC) expansion was carried using media that was previously incubated on a monolayer of fibroblasts and then collected and used to feed stem cells grown on MATRIGEL™-coated dishes. For the next passage, after confluence, the hESCs were split (diluted) 1:4 and fed for 7 days with a media that can include DMEM:F12 1:1, B27 supplement 1×, L-Glutamine, Insulin 10 ug/ml, Na selenite 5 ng/ml, Progesterone 10 ng/ml. After one week, hESC cell colonies were dissociated from the MATRIGEL™ substrate with collagenase IV 1 mg/ml for 5 minutes at 37° C. (Gibco-Invitrogen, Invitrogen, Carlsbad, Calif.), rinsed with DMEM, detached with a cell scraper from the flask surface and placed with the media used above, in ultra-low binding 6-well plates (Fisher Scientific, Pittsburgh, Pa.). A 75 cm$^2$ flask cultured with stem cells to a 70-100% confluence was subjected to enzymatic dissociation and the dissociated cells were resuspended with 30 ml inductive media and distributed in a multi-well plate, with 5 ml of cell suspension in each well, after a gentle trituration of the stem cell clusters by aspirating with a 10 ml serological pipette, up and down, for approximately 2-3 times. The media was supplemented with bFGF 10 ng/ml and 10 µM retinoic acid. Medium was replaced daily for 5 days as follows: the content of each plate was pooled in a 50 ml sterile centrifuge tube and spun at 200×g for 3 minutes. The supernatant was aspirated and replaced with 30 ml fresh media containing the supplements. The pellet was very gently resuspended, so as to not break the clusters, and immediately redistributed in wells, with 5 ml in each well.

For the next 16 days, the cultures were exposed to serum-free media supplemented with bFGF 10 ng/ml. The cellular aggregates reassemble spherical formations, some with tendency to attach to other cells and to form larger complexes or clumps of cells. Media was replaced three times a week, on Monday, Wednesday and Friday, using the same procedure or using a procedure where the cells were left for 5 minute to sediment, and aspirating the supernatant.

On day 28 neurospheres are plated on Matrigel-coated 75 cm square plastic flasks, with each 6 well plate being transferred into one Matrigel-coated 75 cm square plastic flask. The cells migrate and form a monolayer of flat cells and some multilayered clusters can be observed where the neurospheres had originally adhered. The cellular morphology resembled flat triangular cells, and some with unipolar or bipolar short extensions. Cells were characterized at this time point for markers characteristic of the motor neuron precursor (pMN) domain including transcription factors Pax6 and Olig1/Olig2, tubulin marker Tuj1, and also screened for contaminants including glial cell markers GFAP (glial fibrillary acidic protein, an intermediate filament protein found in glial cells such as astrocytes) and S100 (an EF-hand calcium binding protein that interacts with GFAP). Serum-free media was supplemented with bFGF 10 ng/ml, and replaced every other day.

One week later, the cultures were treated with Trypsin-EDTA (Gibco-Invitrogen) and before complete dissociation the flask is shaken leaving some contaminant astrocytes attached to the flask. The cells were split 1:2 and replated in flasks, well plates, or imaging chambers, that had been coated with Matrigel 1:50 or laminin 10-20 µg/ml.

Characterization

Cultures plated on laminin substrate in imaging chamber slides (NUNC™ brand). After 2 days, slides were fixed in 4% paraformaldehyde and screen to detect common neuronal markers including NeuN (neuronal nuclei specific protein) and Tuj1 (a neuronal filament marker) and specific motor neuron markers including: HB9, Ach, Isl1, Lhx3 and Lim1. Cell cultures are assayed for the astrocyte marker GFAP, the oligodendrocyte markers O4, and the microglial marker OX42. Calcium imaging of late stage motor neuron progenitors indicates an absence of calcium channel activity that is characteristic of mature functional motor neurons. Thus, the late stage motor neuron progenitor population is uniquely characterized by the expression of the motor neuron markers HB9, Ach, Isl1, Lhx3. and Lim1 and the absence of calcium channel activity.

Late stage motor neuron progenitors that have been cultured on an astrocyte monolayer for at least 14 days in the absence of growth factors express HB9, Ach, Isl1 and calcium channel activity, characteristic for a mature phenotype and differentiating them from the late stage motor neuron progenitors.

Example 2

Assessment of In Vitro Functionality of MNP Cells

In vitro functionality assessment: Neurons derived from hESCs form neuromuscular junctions and induce muscle contraction when co-cultured with myoblasts. Myoblasts are collected from p0 mice by dissecting a piece of striated muscle from the hip, minced with a scalpel blade and plated in a T75 flask coated with Matrigel 1:50 (or Poly-D-Lisine 20 µg/ml or laminin 10 µg/ml). The media used is serum free, the same used for the neuronal cultures supplemented with 10 µg/ml FGF2 and 20 µg/ml EGF. The myoblasts can be observed emerging from the dissected pieces of muscle the next day and are actively dividing. When they reach a sub-confluent density (70-80%) a mixture of trypsin 0.25% and 100 µg/ml Collagenase IV is used to dissociate the cells from substrate. If necessary, a cell scraper can be used because the myoblasts are very adherent to the substrate. The cells are distributed in imaging chambers pre-coated with Matrigel 1:50 (or laminin 10 µg/ml) at a density of 10×10^3 to 50×10^3. The cultures are fed with serum free media, omitting this time the growth factors bFGF and EGF. In the next day the myoblasts start to fuse and form elongated myotubes of 3 to 10 myoblasts in length. The myoblast cultures are left for another 24 hours, then the chambers are seeded with the motor neurons cultivated following the above protocol plus another 2-4 weeks on a monolayer of astrocytes. The neurons are gently scraped and transferred to the myocyte cultures, without enzymatic dissociation. The cultures are fed with the serum free medium. Identification of agrin, acetylcholine receptor α7, neural agrin, synaptophysin and myotube contraction confirmed functionality of hESC-derived motor neurons by establishing functional neuromuscular junctions.

Example 3

Production of MNP Cells

An additional procedure for deriving motor neuron progenitor (MNP) cells from human embryonic stem cells (hESCs) is described detail in the present example.

Derivation of Motor Neuron Progenitors From hESCs

The human embryonic cell cultures were fed daily and passaged weekly in 75 cm² plastic flasks. The cultures were maintained in commonly used mouse embryonic fibroblast (MEF) conditioned media (CM). The CM media contains, as previously described: KO-DMEM, 20% KO-Serum replacement, Non essential amino acids (1×), L-Glutamine (2 mM), β-mercaptoethanol (100 µM), bFGF (5 ng/ml). This composition was incubated overnight on a confluent and mitotically inactivated mouse embryonic fibroblast culture. Ten (10) ng/ml bFGF was added prior to use for the culture of human embryonic stem cells. This media supports the pluripotency of hESCs, but it also contains many uncharacterized cytokines and growth factors with unknown roles in hESC differentiation. Therefore, a defined media was used that contained components that do not inhibit neuro-ectodermal differentiation, while maintaining the expansion of undifferentiated cells (Table 2).

TABLE 2

Novel hESC Media Composition

| Component | Vendor | Cat # | Vol used | Stock Conc. | Final Conc. |
|---|---|---|---|---|---|
| DMEM/F-12 low osmolality | Gibco | 12660-012 | 467.5 ml | 1x | 1x |
| Non essential amino acids | Gibco | 11140 | 5 ml | 100x | 1x |
| Glutamax (dipeptide L-glutamine) | Gibco | 35050 | 5 ml | 100x | 1x |
| Pyruvate | Gibco | 11360 | 2.5 ml | 100x | 0.5x |
| Human Albumin | Sigma | A1887 | 12.5 ml | 20% | 0.5% |
| Ethanolamine | Sigma | 411000 | 5 µl | 2 mg/ml | 20 µg/ml |
| Insulin | Sigma | I8405 | 500 µl | 5 mg/ml | 5 µg/ml |
| Transferrin | Sigma | T0665 | 250 µl | 20 mg/ml | 10 µg/ml |
| Selenite | Sigma | S9133 | 50 µl | 10 ug/ml | 1 ng/ml |
| T3 | Sigma | T0397 | 50 µl | 0.4 mg/ml | 4 ng/ml |
| Beta mercapto ethanol | Sigma | M7522 | 35 µl | 1.43M | 100 µM |

After one or two passages in the defined hESC media, motor neuron differentiation was initiated by replacing the media and substrate. In order to allow the hESC to adapt to Motor Neuron Media (Table 3), and in order to minimize cells death induced by the change to different media, cells were transferred from the hESC media to a media containing 50% of defined hESC media (Table 1) and 50% Motor Neuron (MN) Media (Table 3). This day was considered to be Day 0 in the Motor Neuron Differentiation process.

TABLE 3

Motor Neuron (MN) Media Composition

| Component | Vendor | Cat # | Vol used |
|---|---|---|---|
| DMEM high glucose | Gibco | 11965 | 500 ml |
| DMEM/F-12 low osmolality | Gibco | 12660-012 | 500 ml |
| ITS | Gibco | 51500-056 | 10 ml |
| B27 supplement mix with Vit. A | Gibco | 17504-044 | 20 ml |
| 0.5M MgCl₂ | Sigma | M7304 | 1000 µl |
| Glutamax (dipeptide L-glutamine) | Gibco | 35050 | 5 ml |

On day 1, after the adaptation to Motor Neuron Media, cells were 90% to 100% confluent and were dissociated into non-adherent conditions. The non-adherent conditions, together with the presence of well-defined factors in Motor Neuron media are required to induce the motor neuron fate. Approximately the same surface area and media volume is used for the non-adherent, floating cultures as well as for the adherent stem cell culture. Dissociation of hESC was performed by treatment with Collagenase IV (Gibco-Invitrogen, Carlsbad, Calif.), 1 mg/ml for approximately 5 minutes at 37° C., rinsed with DMEM, detached with a cell scraper from the flask surface and resuspended in Motor Neuron Media. The cell suspension was transferred into ultra-low binding 75 cm² plastic cell culture flask (Corning).

These non-adherent hESCs were fed daily with Motor Neuron Media supplemented with 10 ng/ml bFGF and 10 µM retinoic acid (RA) dissolved in DMSO for 7 days (Days 1-7). Sphere-like agglomerates of motor neuron progenitors, to be known as "neurospheres," could be observed after 5-6 days of differentiation. Media was replaced daily by allowing the cell agglomerates to settle to the bottom of a conical tube for approximately 15 min, or by gentle centrifugation for 3 minutes at 100×G, and aspirating the supernatant and re-filling the volume to 25 ml of fresh MN media.

After the 7 days of the retinoic acid treatment period, and for the next 12 days (Days 8-19), the culture was allowed to expand and further differentiate. As the cells underwent differentiation, neurospheres increased in size, and the smaller under-differentiated clumps eventually disintegrate or get removed in process of media change. Motor Neuron Media supplemented with only 5 ng/ml of bFGF is used for next 12 days and the media was changed every other day (or on differentiation days 8, 10, 12, 14, 16 and 18) by allowing the spheres to settle to the bottom of a conical tube or by low speed centrifugation.

On day 20, neurospheres were resuspended in fresh MN media and plated on Matrigel-coated 75 cm$^2$ plastic flasks, allowing them to settle down and attach to adherent surface. The larger spheres (neurospheres) were gently dissociated by repeated aspiration with a serological pipette. Within 5-7 days, the cells migrated and formed a high density layer of cells with epithelial morphology. Cells were allowed approximately 7 days to grow and populate the flask (Day 20-27). On day 27-28 the cultures were dissociated using trypsin and re-plated at 1:2 ratio in flasks coated with MATRIGEL™ or laminin-containing substrate.

At the same time, an aliquot of the cells were plated on imaging slides and grown for several days. Immunohistological analyses were performed for markers of motor neurons (HB9) and hESC contaminants (OCT4). In addition, we tested for presence of other neuronal cells, such as astrocytes (GFAP) as well as for cells of other lineages, specifically mesodermal (SMA) and endodermal cells (AFP). Cells were tested for karyotypic stability and for mycoplasma absence. The phenotype of the population of cells is represented in Table 4. Only those cell populations wherein the parameters met the specifications shown in Table 4, were are released for further use.

TABLE 4

Cell parameters for motor neuron cell release

| PARAMETER | SPECIFICATION |
|---|---|
| Karyotype | 46, XX or 46, XY |
| HB9 | $\geq$75% |
| OCT4 | $\geq$2% |
| GFAP | $\geq$15% |
| SMA | $\geq$4% |
| AFP | $\geq$4% |
| Mycoplasma | Negative |

At this stage, cells were early stage motor neuron progenitors (early stage MNPs) that further matured with prolonged culturing and produce more mature motor neuron progenitors (late stage MNP cells) that morphologically resemble typical neurons with small cell bodies and long branches. These late stage MN progenitors (late stage MNP cells) can be successfully plated in other formats than 75 cm$^2$ plates, such as 96 well plate format, and transported live to the end user. These cells can be used for animal transplantation, as described below.

As described in the following Example, some cells were plated in 96 well plates coated with Matrigel, Poly-L-Lysine and laminin or laminin only with densities from $10^3$ to $10^4$ cells per well. Plates containing plated MN progenitors were cultures for another 7 days or shipped to a remote location to assess viability and phenotype.

Example 4

Transportation of Live MNP Cells

Transportation of live MNP was tested using a few different carriers for overnight delivery from California to US territories or Europe over two consecutive days. The flasks containing the adherent cultures were topped with media to avoid foaming and mechanical dissociation of attached cells. Then the flasks were packed in absorbent cushioning material and placed in biohazard labeled bags. The flasks were finally surrounded by phase exchange isothermal packs to ensure a constant temperature range of between 20-30° C. Temperature recording devices were packed with the cell containers to record the shipping parameters.

Upon receipt, the packaging containing the cells (in flasks or multi-well plates) was inspected for integrity, leakages and/or other damage. Data from data logger was received and analyzed to show the temperature variations during the shipment. Once cell flask was inspected visually for damages and leaks, cells were inspected under an inverted microscope for contamination and cellular debris. Media was completely removed and replaced with 0.5 ml/cm$^2$ of fresh media at room temperature. After the media change, flask was placed in the $CO_2$ incubator at 37° C.

Example 5

Preparation of a High-Purity Population of Viable MNP Cells

For animal transplantation, a high-purity population of viable MNP cells was prepared as described below. Motor neuron progenitors (MNP cells) plated at day 28 on adherent substrate, were dissociated using trypsin replacement 0.05 ml/cm$^2$ TrypLE (Invitrogen, Carlsbad, Calif.). Cells were incubated for three to five (3 to 5) minutes at 37° C. until all the cells were detached. MNPs were collected into appropriate centrifuge tube and the volume is adjusted to 0.5 ml/cm$^2$ of the original culture with fresh Motor Blast media. Cells were centrifuged for three (3) minutes at 200 rcf, supernatant is aspirated and media is replaced with fresh Motor Blast media to 0.5 ml/cm$^2$ of the original culture surface (for example 35 ml for a 75 cm$^2$ flask). This washing procedure was repeated two more times. To determine the cell number, a 50 μl aliquot was removed from the cell suspension and placed in a 1.5 ml centrifuge tube containing 50 μl Trypan blue. The numbers of viable and non-viable (dead) cells was determined by counting the non-stained cells (viable cells) and the blue-stained cells (non-viable, dead) in an 8 mm$^2$ area, using a hemacytometer according to the Trypan Blue exclusion method. The final concentration of cells was determined using the formula shown in the "MotorGraft Transplant Worksheet" presented as Table 5.

After determining the concentration of cells, the cell suspension was placed in an ultra low binding culture dish and placed in the incubator to rest. It was determined that flasks should not be moved for a minimum of six (6) hours and for a maximum of twenty (20) hours. After overnight resting, the viable cells were organized into floating microspheres. Any isolated floating cells that were not organized into micropsheres were considered nonviable and were removed in three consecutive washes, to ensure 100% viable cells having the desired properties.

First, cells were collected into a 50 ml sterile centrifuge tube and centrifuged for three (3) minutes at 100 rcf. Supernatants from each wash were collected into separate tubes and tal on a sterile surface. One syringe load should be sufficient for 4 to 5 transplants, but the needle should be cleaned with isopropyl-alcohol wipe(s) between animals.

TABLE 5

Motorgraft transplant worksheet table

Flask Label #: _____ Procedure Date: _____

| Materials | Cas No. | Lot No. | Expiration Date |
|---|---|---|---|
| Motor Graft | | | |
| TrypLE | | | |
| Cell Transplant Solution | | | |
| MotorBlast Media | | | |
| Low adherent flask | | | |
| Sterile 1.5 ml vials | | | |
| Sterile 15 ml tubes | | | |
| Sterile 50 ml tubes | | | |

| Step | | | | | | | |
|---|---|---|---|---|---|---|---|
| 1. TrypLE exposure _____ min | | | ☐Wash 1 (3 min) | ☐Wash 2 (3 min) | | | |
| 2. Initial Count (IC): | Vol. | | 1<br>3<br>5<br>7 | 2<br>4<br>6<br>8 | Dilution | Average | Total |
| 3. Time placed at rest: | | | | | ☐Resting time <20 hours | | |
| 4. Time of dose preparation: | | | | | | | |
| 5. ☐ Wash 1<br>Discard Count 1 (D1): | Vol. | | 1<br>3<br>5<br>7 | 2<br>4<br>6<br>8 | Dilution | Average | Total |
| 6. ☐ Wash 2<br>Discard Count 2 (D2): | Vol. | | 1<br>3<br>5<br>7 | 2<br>4<br>6<br>8 | Dilution | Average | Total |
| 7. ☐ Wash 3<br>Discard Count 3 (D3): | Vol. | | 1<br>3<br>5<br>7 | 2<br>4<br>6<br>8 | Dilution | Average | Total |
| 8. Total Viable Cells (TVC) = IC − (D1 + D2 + D3) | | | | | = | | |
| 9. Volume of transplant vehicle added = TVC/$10^6$ | | | | | =<br>(µl) | | |
| 10. Measured pellet volume (MV) | | | | | =<br>(µl) | | |
| 11. Final concentration needed (FC) | | | | | ☐25,000<br>(cells/µl) | ☐125,000 | |
| 12. Final volume at desired concentration (FV = TVC ÷ FC) | | | | | =<br>(µl) | | |
| 13. CTS added to obtain the desired concentration (FV − MV) | | | | | =<br>(µl) | | | the total number of particles was counted and recorded separately. Total number of viable cells contained in the microspheres was determined by subtracting from the total counted cells (viable and nonviable) in the previous day, the cells (viable and nonviable) discarded in the washes. Total number of viable cells was determined using formula in FIG. 5.

From these measurements the total volume needed in order to achieve 25,000 cells or 125,000 cells/µl, (FV-MV) was calculated, and the required amount of cell transplant solution was added to the desired final volume. After this, the cells were placed on a mixing chilled dry bath, set to 7° C. and 200 rpm. Cells are stable for 2 h, after which any unused cells should be discarded.

At this point, cells were ready to be loaded in the transplant syringe (10 µl Hamilton syringes with removable metal needles, gauge 33). Prior to loading the syringes, needle and syringe were properly washed first with 10 µl of Cell Transplant Solution and then with 10 µl of 70% ethanol in water. This process was repeated two times and cells are loaded in the injection syringe in volume of 10 µl of cell suspension. Between animal manipulations, the syringe was kept horizon- Example 6

Transplantation of MNP Cells Into the Spinal Cord of the G93A SOD1 Mouse Model of ALS In order to evaluate the survival of the transplanted cells and integration into the host, motor neuron progenitor (MNP) cells were transplanted into the spinal cord of SOD G93A mice. The G93A SOD1 mouse has been bred for the purposes of studying motor neuron disease. The SOD1 G93A is a transgenic mouse carrying a transgene that codes for the human SOD1 mutation that leads to a familial form of ALS. This mutation converts the glycine at amino acid position 93 to an alanine and hence termed as SOD1 G93A mice. The gene is driven by the natural SOD1 promoter and is expressed ubiquitously in all tissues. This mutation is a gain-of-function mutation, and transgenic mice carrying this mutation over its existing normal mouse SOD1 gene show a neurodegenerative phenotype even in heterozygous state. The pathology and progression of the disease in mice is similar to the familial ALS and SMA and also mimics the sporadic form of ALS whose etiology is largely unknown. For these reasons, it is considered an excellent model for discovering drugs for human ALS or SMA. The only approved drug for ALS that showed a 10% extension in life of ALS patients, showed a similar effect in this mouse model.

To test the hypothesis that hESC-MNPs will survive and integrate into the SOD1 mouse model of ALS and SMA, an increasing dose of hESC-MNPs were injected intraspinally following laminectomy. The animals were survived for two time points—28 and 56 days (as described in Table 6). Cage side observations were conducted daily: clinical signs of toxicity and body weight changes were monitored. At the end of the study terminal collection of the following organs was performed: brain, spinal cord, blood, liver, muscle, spleen and lung.

TABLE 6

Animal groups for transplantation of MNP cells

| Cohort | 'n' | Treatment | Duration |
| --- | --- | --- | --- |
| SOD1, 50,000 cell injection | 4 males, 4 females | 1 µL at 50,000 cells/ul | 28 days |
| SOD1, 100,000 cell injection | 4 males, 4 females | 1 µL at 100,000 cells/ul | 28 days |
| SOD1, 100,000 cell injection | 4 males, 4 females | 1 µL at 100,000 cells/ul | 56 days |
| SOD1, Sham Operated | 2 males, 2 females | 1 µl of vehicle | 28 Days |
| SOD1, Sham Operated | 2 males, 2 females | 1 µl of vehicle | 56 Days |
| Wild-type, 100,000 cell injection | 4 males, 4 females | 1 µl of vehicle | 28 Days |

Each animal was tested for deep anesthesia by pinching the tail and checking corneal reflexes, and prepared for surgery. A laminectomy was performed at thoracic level T9 across two vertebral bodies. For transplantation, 32G Hamilton needles with 30° bevels were used. The syringes were back-filed using a 1 ml insulin syringe and a 26G needle. The Hamilton syringe was kept horizontal in between injections to prevent sedimentation of the cells. Each load of 10 µl of cell suspension was used to inject 4-5 animals, than the leftover discarded, the syringe cleaned, sterilized and reloaded with a new batch of cells.

At the end of study, immunohistochemical analyses on animal spinal cord tissue were performed to determine the identity and localization of transplanted cells. Human cells in the mouse spinal cord tissue were detected by anti-human nuclear labeling of transplanted cells (hESC-MNPs) using anti-human-nuclear-protein-antibody and methyl-green counterstain, and the images were examined at 10× and 20× for qualitative and quantitative assessments. The human cells were detected at the implantation site and in the ventral horn of the spinal cord, in large numbers and in each of the analyzed grafted animals. Cells distributed approximately 1.5 mm from the injection site. The data indicate that the implanted hESC-MNPs migrated to the anatomically correct site. The data also indicated that hESC-MNPs retained their identity when transplanted into mice.

What is claimed is:

1. A method of generating a high-purity population of late stage motor neuron progenitor cells, wherein the population has a purity of greater than about 65% late stage motor neuron progenitor cells, comprising:
    (a) neuralizing a culture of pluripotent stem cells by culturing pluripotent stem cells in a growth media that contains beta fibroblast growth factor (bFGF) and that lacks bone morphogenic protein (BMP), and that is supplemented with one or more of albumin, a fatty acid, a thyroid hormone, a vitamin, a trace mineral, insulin and transferrin;
    (b) ventralizing the neutralized cell population of step (a) comprising culturing the cell population under non-adherent conditions in a motor neuron media supplemented with retinoic acid and beta fibroblast growth factor (bFGF) for at least about five days,
    (c) incubating the ventralized cell population of step (b) comprising culturing the cell population in growth media with bFGF without retinoic acid to promote formation of neurospheres,
    (d) selecting the neurospheres;
    (e) expanding neurospheres on an adherent substrate to form a layer of cells comprising a population of cells comprising greater than about 65% late stage motor neuron progenitor cells, wherein said late stage motor neuron cells express markers of the motor neuron HB9, Ach, Isl1, Lhx3, and Lim1, but lack a functional calcium channel.

2. The method of claim 1, wherein the growth media is a serum-free media.

3. The method of claim 1, wherein the motor neuron media is a serum-free media.

4. The method of claim 1, wherein selecting the neurospheres comprises gravitational sedimentation of the neurospheres.

5. The method of claim 1, wherein the population of late stage motor neuron progenitor cells comprises cells characterized by the expression of at least one of a neurofilament marker or a neuronal nuclei specific protein.

6. The method of claim 5, wherein the at least one of a neurofilament marker is at least one of Tuj1, MAP2, and SM132.

7. The method of claim 6, wherein the neuronal nuclei specific protein is NeuN.

8. The method of claim 3, wherein the serum-free growth media comprises non-essential amino acids, dipeptide L-glutamine, pyruvate, human albumin, ethanolamine, insulin, transferring, selenite, and T3 thyroid hormone.

9. The method of claim 3, wherein the serum-free motor neuron media comprises B27 supplement with vitamin A, magnesium chloride, and dipeptide L-glutamine.

10. The method of claim 3, wherein the serum-free motor neuron media is supplemented with retinoic acid at a concentration of between about 5 µM to about 20 uM.

11. The method of claim 1, wherein the bFGF is at a concentration of between about 2 ng/mL to about 20 ng/mL.

12. The method of claim 1, wherein the layer of cells comprising a population of cells having greater than about 65% late stage motor neuron progenitor cells, has a purity of between 65% and 100% late stage motor neuron progenitor cells.

13. The method of claim 1, wherein the contaminant population in the layer of cells comprising a population of cells having greater than about 65% late stage motor neuron progenitor cells, is less than about 35% astrocytes.

14. The method of claim 1, wherein the contaminant population in the layer of cells comprising a population of cells having greater than about 65% late stage motor neuron progenitor cells, is between 0% and about 35% astrocytes.

15. The method of claim 1, wherein the cells do not express one or more of OCT4, GFAP, SMA, or AFP.

16. An isolated population of late stage motor neuron progenitor cells prepared by the method of claim 1, wherein the population of cells comprises greater than about 65% late stage motor neuron progenitor cells and the late stage motor neuron progenitor cells express markers of the motor neuron HB9, Ach, Isl1, Lhx3, and Lim1, but lack a functional calcium channel.

* * * * *